(12) United States Patent
Linares

(10) Patent No.: US 8,211,182 B2
(45) Date of Patent: Jul. 3, 2012

(54) HIP SOCKET WITH ASSEMBLEABLE MALE BALL SHAPE HAVING INTEGRALLY FORMED LIGAMENT AND FEMALE RECEIVER AND INSTALLATION KIT

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 258 days.

(21) Appl. No.: 12/652,227

(22) Filed: Jan. 5, 2010

(65) Prior Publication Data

US 2010/0228355 A1  Sep. 9, 2010

Related U.S. Application Data

(63) Continuation-in-part of application No. 12/649,456, filed on Dec. 30, 2009, and a continuation-in-part of application No. 12/212,141, filed on Sep. 17, 2008, now Pat. No. 7,887,586.

(60) Provisional application No. 60/972,903, filed on Sep. 17, 2007, provisional application No. 61/031,187, filed on Feb. 25, 2008.

(51) Int. Cl.
*A61F 2/32* (2006.01)
*A61F 2/36* (2006.01)

(52) U.S. Cl. .................. 623/22.15; 623/23.4; 623/23.41

(58) Field of Classification Search .... 623/19.11–19.14, 623/22.11, 22.15, 23.39, 23.4, 23.41
See application file for complete search history.

(56) References Cited

U.S. PATENT DOCUMENTS

| | | | |
|---|---|---|---|
| 2,667,644 A | 2/1954 | Johnson | |
| 3,973,277 A | 8/1976 | Semple et al. | |
| 4,483,023 A | 11/1984 | Hoffman, Jr. et al. | |
| 4,501,031 A | 2/1985 | McDaniel et al. | |
| 4,665,951 A | 5/1987 | Ellis et al. | |
| 4,744,793 A | 5/1988 | Parr et al. | |
| 4,778,473 A | 10/1988 | Matthews et al. | |
| 4,792,336 A | 12/1988 | Hlavacek et al. | |
| 4,828,562 A | 5/1989 | Kenna | |
| 4,851,005 A | 7/1989 | Hunt et al. | |
| 4,883,486 A | 11/1989 | Kapadia et al. | |

(Continued)

FOREIGN PATENT DOCUMENTS

WO  2009039164 A1  3/2009

*Primary Examiner* — Thomas J Sweet
*Assistant Examiner* — Jason-Dennis Stewart
(74) *Attorney, Agent, or Firm* — Gifford, Krass, Sprinkle, Anderson & Citkowski, P.C.

(57) ABSTRACT

A hip implant assembly including a spherical shaped ball and an elongated stem. An annular defining rim separates the ball from the stem and abuts, in a maximum inserting condition, over an exterior reconditioned surface of the femur and upon inserting the stem within an interior passageway formed within the femur. A cup shaped support seats the ball in a universally articulating permitting fashion via a flexible and resilient ligament which extends from the ball and is received within a recess passageway of the cup. The cup also includes a mounting surface with a central projecting portion which is in turn resistively fitted within an undercut defined recess formed in the ilium bone in communication with a base surface of the reconditioned acetabulum socket. A corresponding installation kit assists the preparation of the femur and ilium bones defining the hip joint, as well as the installation of the implant body into the upper conditioned femur end and the cup shaped and outer socket support to a reconditioned acetabulum defined in the ilium bone.

17 Claims, 11 Drawing Sheets

U.S. PATENT DOCUMENTS

| | | |
|---|---|---|
| 5,004,474 A | 4/1991 | Fronk et al. |
| 5,078,745 A | 1/1992 | Rhenter et al. |
| 5,171,325 A | 12/1992 | Aulie |
| 5,263,984 A | 11/1993 | Li et al. |
| 5,282,867 A | 2/1994 | Mikhail |
| 5,376,119 A | 12/1994 | Zimmermann et al. |
| 5,389,107 A | 2/1995 | Nassar et al. |
| 5,417,693 A | 5/1995 | Sowden et al. |
| 5,486,197 A | 1/1996 | Le et al. |
| 5,554,194 A | 9/1996 | Sanders |
| 5,571,191 A | 11/1996 | Fitz |
| 5,575,819 A | 11/1996 | Amis et al. |
| 5,676,702 A | 10/1997 | Ratron et al. |
| 5,707,395 A | 1/1998 | Li |
| 5,728,175 A | 3/1998 | Rincoe |
| 5,800,566 A | 9/1998 | Gramnas et al. |
| 5,879,404 A | 3/1999 | Bateman et al. |
| 5,921,358 A | 7/1999 | Gramnas et al. |
| 6,001,106 A | 12/1999 | Ryan et al. |
| 6,010,535 A | 1/2000 | Shah |
| 6,190,411 B1 | 2/2001 | Lo et al. |
| 6,245,109 B1 | 6/2001 | Mendes et al. |
| 6,325,804 B1 | 12/2001 | Wenstrom, Jr. et al. |
| 6,383,223 B1 | 5/2002 | Baehler et al. |
| 6,582,715 B1 | 6/2003 | Barry et al. |
| 6,626,942 B1 | 9/2003 | Edberg et al. |
| 6,645,251 B2 | 11/2003 | Salehi et al. |
| 6,840,962 B1 | 1/2005 | Vacanti et al. |
| 6,939,379 B2 | 9/2005 | Sklar |
| 7,044,983 B1 | 5/2006 | Cheng et al. |
| 7,056,340 B2 | 6/2006 | McKernan et al. |
| 7,066,958 B2 | 6/2006 | Ferree |
| 7,087,091 B1 | 8/2006 | Chen et al. |
| 7,101,398 B2 | 9/2006 | Dooris et al. |
| 7,153,327 B1 | 12/2006 | Metzger |
| 7,175,666 B2 | 2/2007 | Yao |
| 7,329,281 B2 | 2/2008 | Hays et al. |
| 7,331,995 B2 | 2/2008 | Eisermann et al. |
| 7,708,781 B2 | 5/2010 | Scheker |
| 2001/0051831 A1 | 12/2001 | Subba Rao et al. |
| 2002/0013627 A1 | 1/2002 | Geistlich et al. |
| 2003/0130741 A1 | 7/2003 | McMinn |
| 2004/0024460 A1 | 2/2004 | Ferree |
| 2005/0081867 A1 | 4/2005 | Murphy |
| 2005/0187620 A1 | 8/2005 | Pai et al. |
| 2005/0192674 A1 | 9/2005 | Ferree |
| 2006/0058886 A1 | 3/2006 | Wozencroft |
| 2006/0074423 A1 | 4/2006 | Alleyne et al. |
| 2006/0149370 A1 | 7/2006 | Schmieding et al. |
| 2007/0005137 A1 | 1/2007 | Kwak |
| 2009/0039164 A1 | 2/2009 | Herwig et al. |
| 2009/0088865 A1 | 4/2009 | Brehm |
| 2009/0292364 A1 | 11/2009 | Linares |

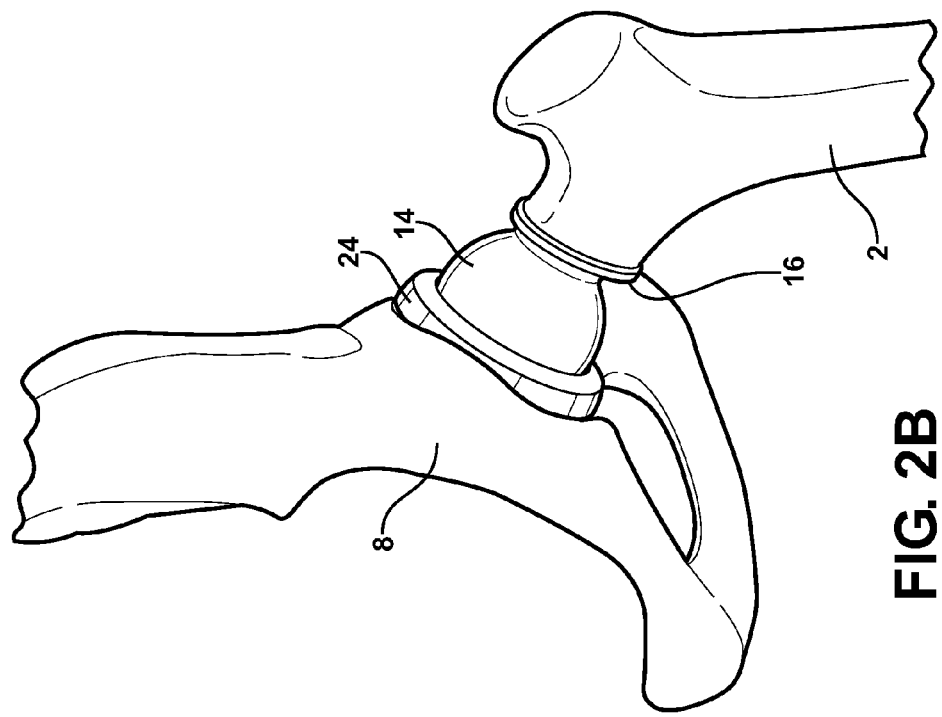
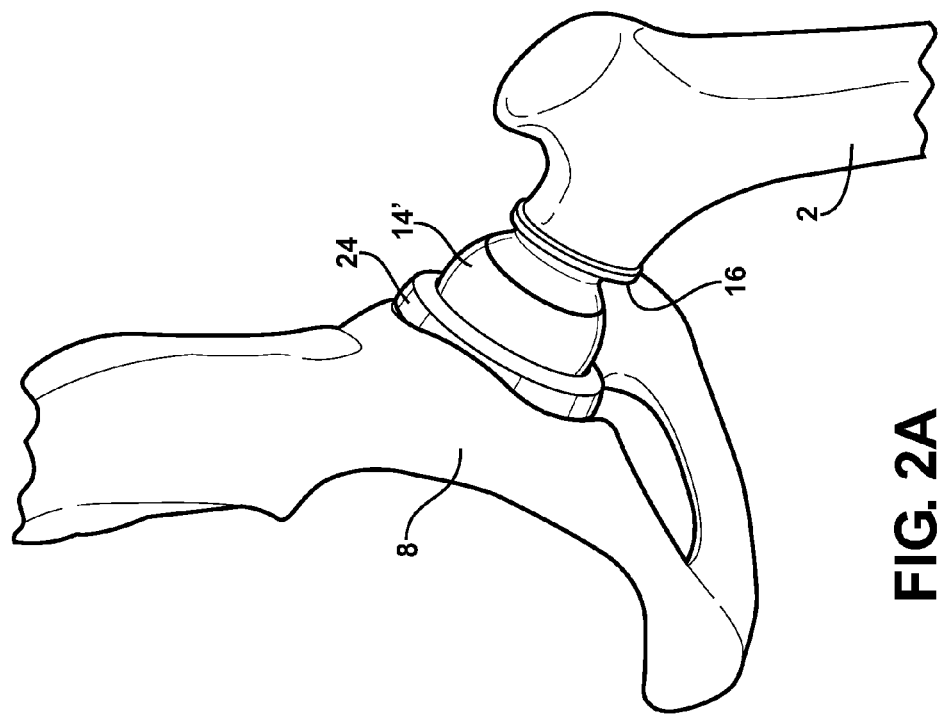
FIG. 2B
FIG. 2A

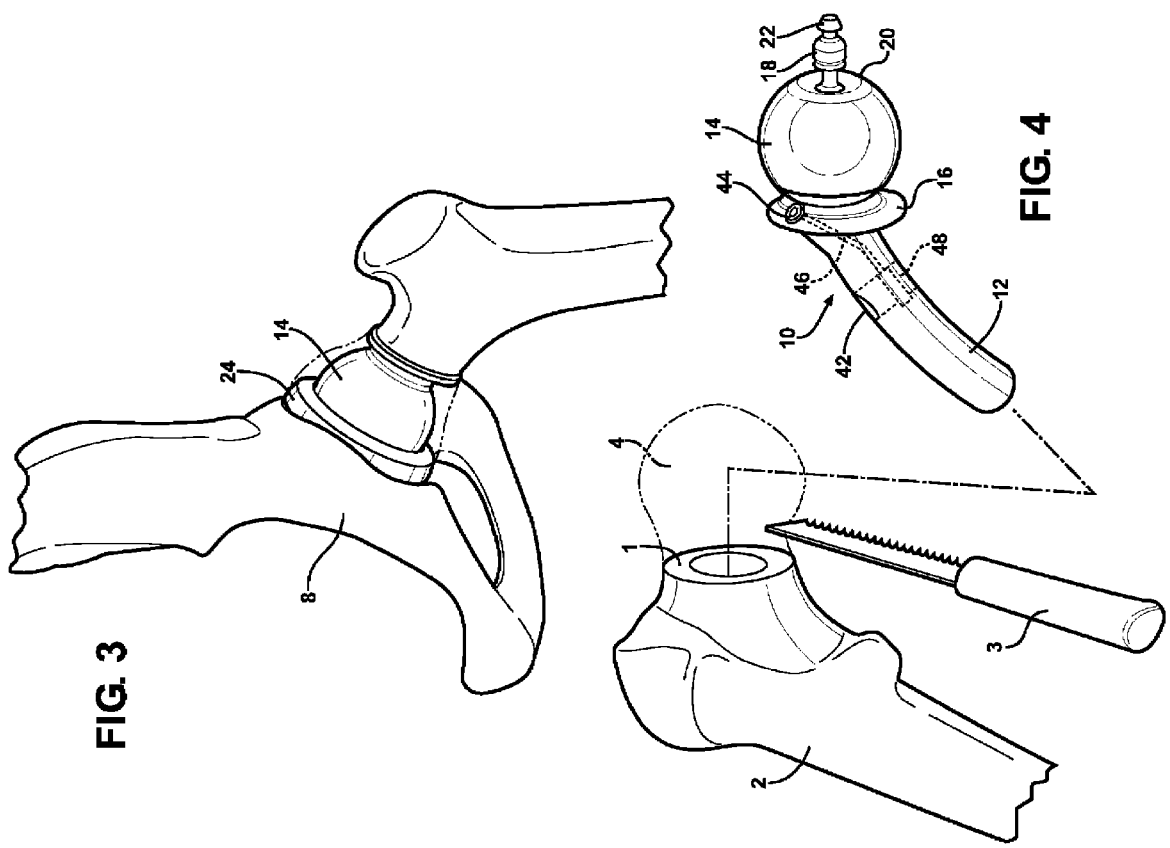

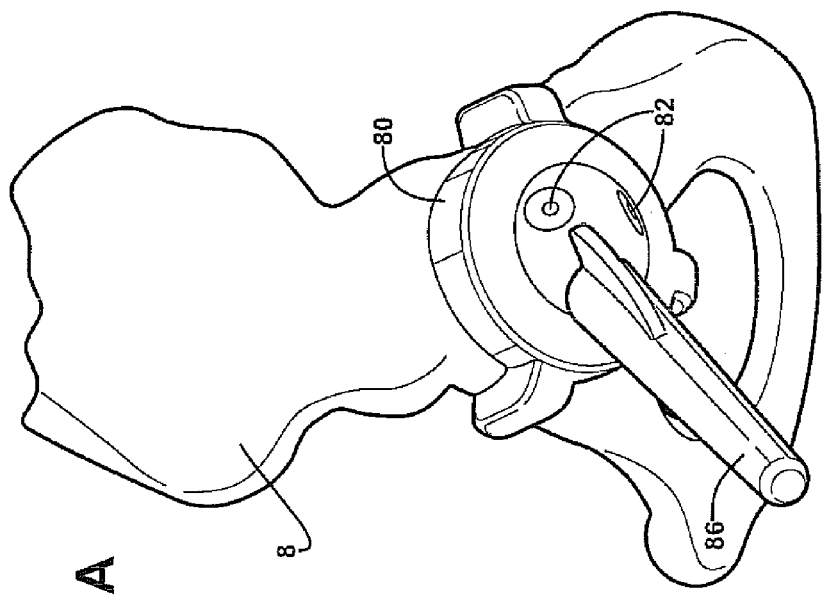
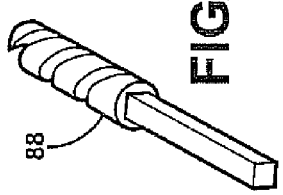
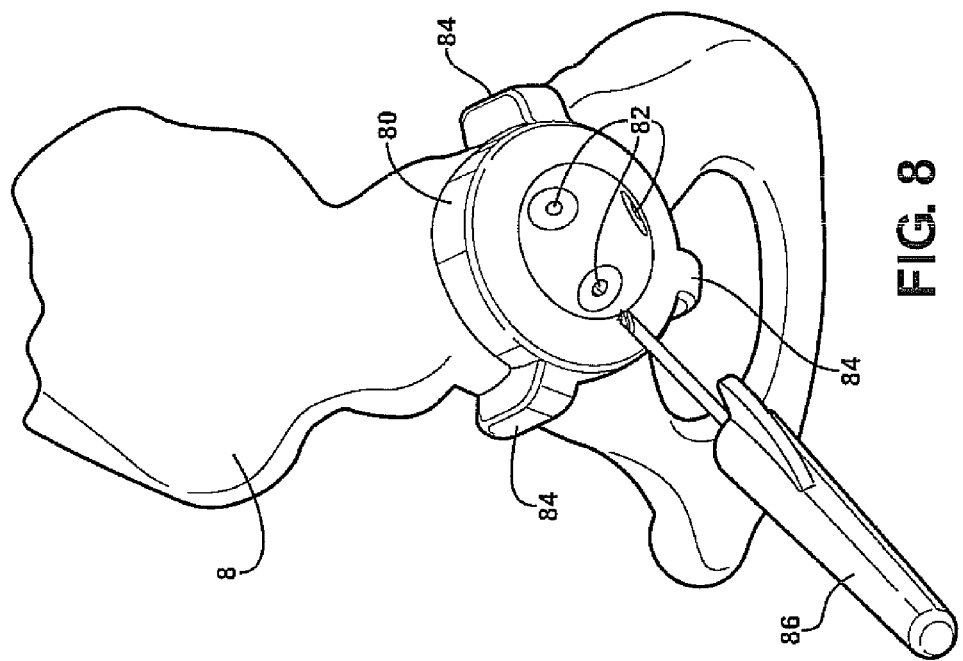

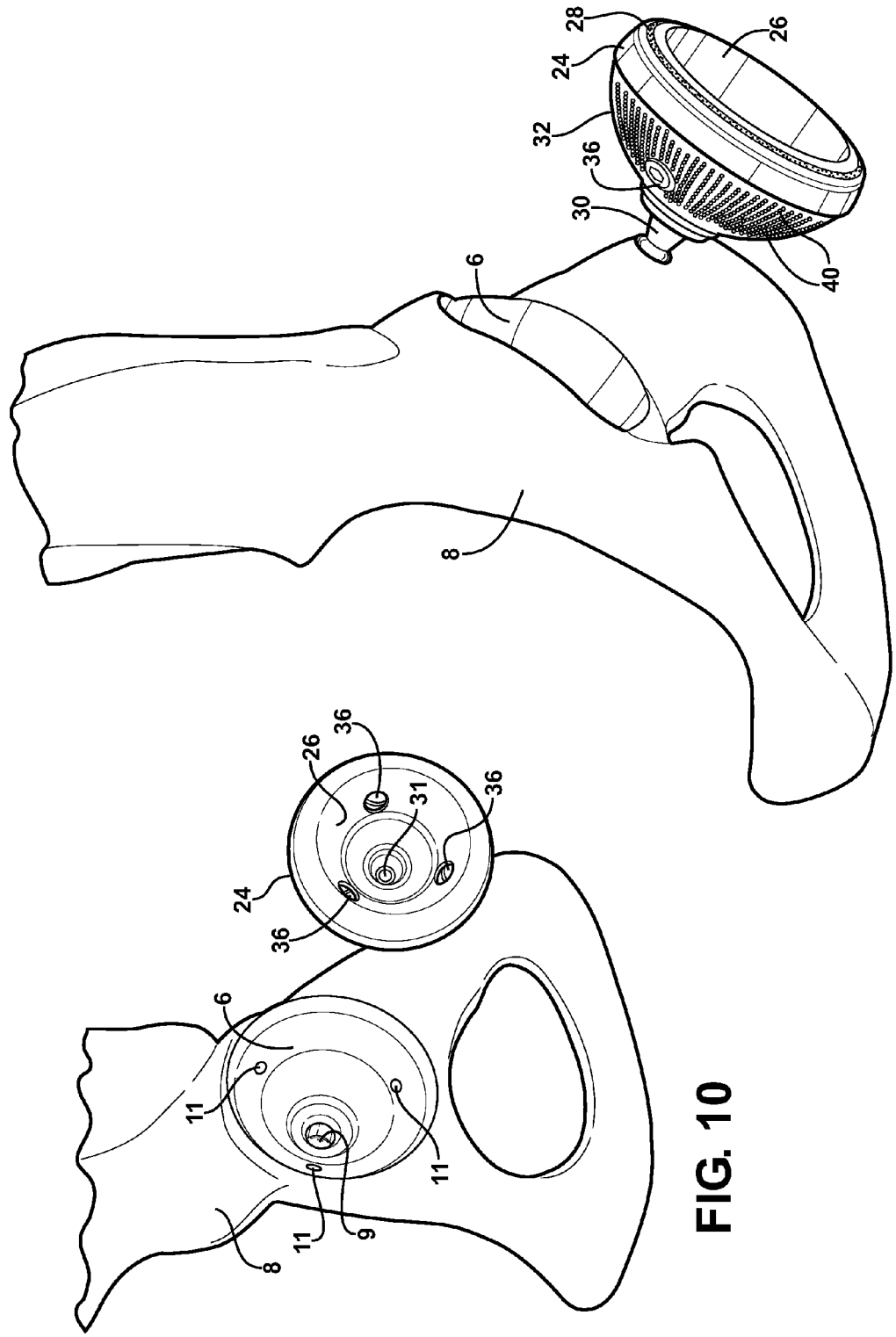

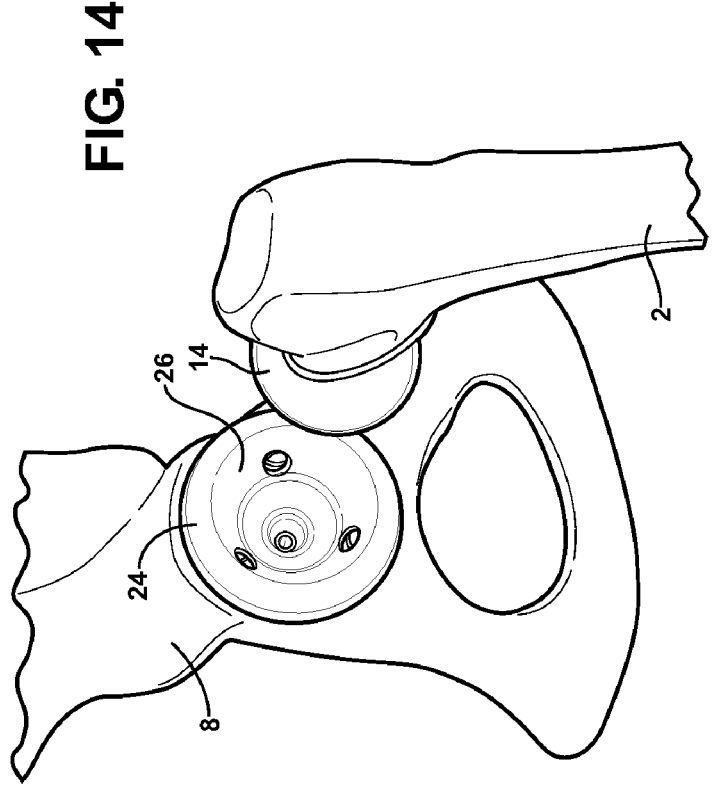

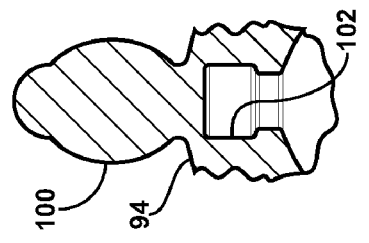
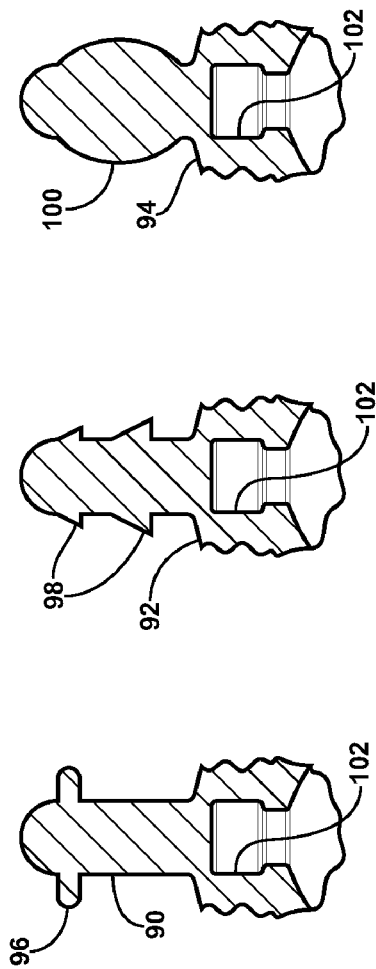
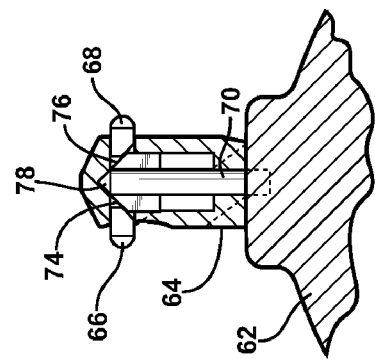
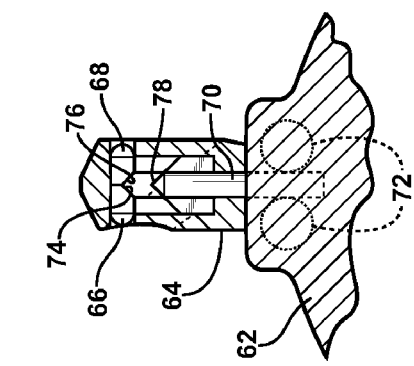

HIP SOCKET WITH ASSEMBLEABLE MALE BALL SHAPE HAVING INTEGRALLY FORMED LIGAMENT AND FEMALE RECEIVER AND INSTALLATION KIT

CROSS-REFERENCE TO RELATED APPLICATIONS

This application is a continuation-in-part of patent application Ser. No. 12/649,456 filed Dec. 30, 2009, as well as a continuation-in-part of application Ser. No. 12/212,141 filed Sep. 17, 2008, which claims the benefit of U.S. Provisional Patent Application Ser. Nos. 60/972,903 filed on Sep. 17, 2007 and 61/031,187 filed on Feb. 25, 2008.

FIELD OF THE INVENTION

The present invention relates generally to replacement assemblies for use in the acetabulofemoral (i.e. hip) joint. More particularly, the present invention teaches a self-contained and replaceable articulating hip utilized in a hip arthroplasty procedure and incorporating an integrally formed ligament interconnecting the spherical ball and outer cup shaped support. A corresponding an installation kit assists in the reconditioning preparation of the femur and ilium bones defining the hip joint, as well as the installation of the implant body into the upper conditioned femur end and the outer socket defining and cup shaped support to the reconditioned acetabulum defined in the ilium bone.

BACKGROUND OF THE INVENTION

The prior art is documented with various types of hip replacement assemblies. These typically include either the removal and/or refashioning of the insertable head associated with the thigh or upper femur bone along with the receiving acetabulum socket defined in the pelvic area located ilium bone. Such replacement hip assemblies can also incorporate artificial or synthetic implant components, however their relative large size contributes to an attendant degree of installation effort and patient discomfort associated with its surgical implantation.

SUMMARY OF THE INVENTION

The present invention discloses a hip implant assembly including body exhibiting a substantially spherical shaped ball and an elongated stem. An annular defining rim separates the ball from the stem and abuts, in a maximum inserting condition, an exterior surface of a reconditioned femur upon inserting the stem within an interior passageway associated with the femur.

A cup shaped member exhibits a concave defining face and includes an interior communicating passageway configured for receiving in a resistive fitting fashion a flexible and resilient ligament associated with the ball, thereby establishing a degree of universal articulating and seating support to the ball within the cup. The cup is in turn affixed to a previously reconditioned acetabulum socket associated with an ilium bone, and in which a further central positioned hole with an undercut feature is created for receiving a like configured and central projection associated with a reverse and convex inserting face of the cup support, such projection supporting the interior passageway for receiving the ligament.

Additional features include the body and support being constructed of any type of plastic, metal or admixture thereof, and an inner remote end of the stem being cored or otherwise recess machined in order to promote the in-growth of marrow within the and around the stem. The cup shaped support may also include a softer and inner/arcuate shock absorbing layer extending in embedded fashion between an inner facing surface and an outer facing surface seating against the acetabulum socket. The annular extending flange of the body may also constructed of a softer grade material than either the stem and ball to assist in shaping and form fitting about an exposed reconditioned surface of the upper femur. A socket anchor constructed of a flexible material with a radially expansible/protruding barb extension is fitted into the previously formed undercut recess defined in the acetabulum and receives the central projection associated with the reverse and convex inserting face of the cup support.

An outwardly displacable anchor is further defined within the extending stem of the femur implanted body and is actuated by a rotatable input to screw surface mounted in said annular flange. A series of interior and interconnected linkages are incorporated into the stem of the body and transfer a rotatable input applied to the annular flange located and surface exposed screw to outwardly displace the anchor into biasing contact with the interior of the femur, causing the flange to be drawn tight against the reconditioned surface of the femur. A subset variant also includes the one piece ball and supporting stem reconfigured as a pair of threadably engageable components, such that the ball includes an externally threaded shaft end which is threadably engaged with an inner threaded surface associated with a mating interior passageway of the stem and in proximity to the annular flange.

An associated installation kit for assisting the preparation of the femur and ilium bones defining the hip joint, as well as the installation of the implant body into the upper conditioned femur end and the stationary cup shaped and outer socket defining support to a reconditioned acetabulum defined in the ilium bone, includes a saw for removing a damaged bulbous shaped head associated with the femur and in order to reveal a generally annular shaped receiving face which communicates an interior extending passageway. A hand held grinder exhibiting a hemispherical shaped and rotatably driven grinder bit reshapes the acetabulum socket to match a mounting surface associated with the outer socket support.

The grinder further includes a central projecting blade for creating a hole in a base of the acetabulum. A subsequently outwardly protruding and centrally located pair of undercut profile defining blades are configured within the central projecting blade and are incrementally actuated for creating a successive undercut configuration within the access hole formed in the reground acetabulum, and which is subsequently engaged by the central base projection associated with the cup.

A drill fixture template is mounted to the ilium bone and overlays the reconditioned acetabulum, the template including a plurality of apertures arranged in a desired pattern array. A drill is insertable in succession into through each of the apertures defined in the template and in order to create an initial hole within the acetabulum. Upon aligning the cup over the reformed acetabulum, and concurrent with the central projection fitting within the undercut created recess, a further plurality of screws are provided and install through apertures defined in the arcuate body of the cup which align with the holes formed by the drill template and in order to anchor the cup within the reformed acetabulum.

Additional features include the grinder blades associated with the hemispherical surface of the grinder exhibiting individual incising blade portions arranged in a longitudinal arrayed pattern. A three dimensional open interior created within a tool head of the grinder between a base and the hemispherical bit providing for collection of bone shavings and debris, these vacuum removed for storage within a waste chamber located in a rear handle. The drill template further exhibits edge extending engagement tabs temporarily mounted to specified surface locations of the ilium bone.

BRIEF DESCRIPTION OF THE DRAWINGS

Reference will now be made to the attached drawings, when read in combination with the following detailed description, wherein like reference numerals refer to like parts throughout throughout the several views, and in which:

FIG. 2A is an assembled perspective view of the implant assembly shown in FIG. 1B;

FIG. 2B is a corresponding assembled perspective view of the implant assembly shown in FIG. 1A;

FIG. 3 is an illustration largely similar to that shown in FIG. 2B and by which the combined ball and socket is shown in comparison to a dimension in phantom illustrative of an original ball socket and to which the implant assembly closely matches in dimension;

FIG. 4 is a partially exploded view of the upper femur illustrating in phantom outline the removed ball and further showing the implant assembly including insert stem and spherical shaped ball mounted to the reconditioned femur end;

FIG. 8 is an illustration of a successive installation step following the rotary grinder of FIGS. 6 and 7 in the arthroplasty procedure and by which the a drill fixture template is mounted to the previously refashioned cavity, the fixture including an array of apertures for receiving a further drill in order to create a pattern within the recessed interior of the previously reformed socket;

FIG. 8A is a further partial illustration of a modified drill exhibiting a bit attachment end;

FIG. 9 illustrates a variant of the drill in which a vacuum feature is incorporated for removing debris into a waste chamber incorporated into the fixture;

FIG. 10 is a succeeding illustration in which the drill fixture template is removed and the cup shaped support is positioned over the acetabulum with its arrayed pattern of receiving holes aligning with the drill holes previously made into the ilium bone and prior to the installation of anchors;

FIG. 11 is a rotated perspective view to that shown in FIG. 10 and which illustrates a central engaging projection associated with the three dimensional mounting face of the cup shaped support for engaging within the previously drill undercut recess;

FIG. 14 is a rotated perspective of the view shown in FIG. 13;

FIGS. 15-17 illustrate a succession of differently configured socket anchors exhibiting side expansible or protruding barbs resistively installed into a previously formed undercut profile for subsequent receipt of the flexible and resilient ligament;

FIG. 18 is a partial illustration in cutaway of the central protruding blade associated with the rotary grinder and illustrating the laterally displaceable blade undercut portions in an initial retracted position during formation of the primary drill hole; and FIG. 19 is a succeeding illustration in which the laterally displaceable blade portions are progressively and incrementally actuated to form the desired undercut profile.

DETAILED DESCRIPTION OF THE PREFERRED EMBODIMENTS

Referring now to the several illustrations, the present invention teaches a self-contained and replaceable articulating hip utilised in a hip arthroplasty procedure. The ball, cup shaped socket/receiver and associated stem components can be constructed of any type of plastic, metal or admixture according to any desired ratio or percentage. As will be also described, the individual implant components can be provided with varying hardness, such as which maximizes comfort and wear, and it is further understood that the present assembly provides for a maximum degree of implant efficiency, universality in use and degree of comfort to the patient.

Figure 5A:
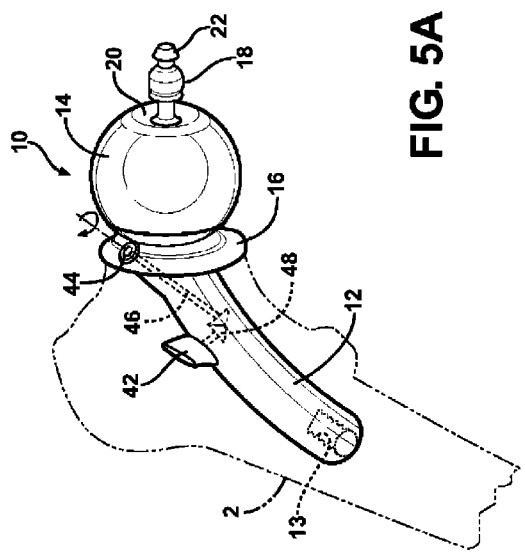
FIG. 5A is a successive assembled view to that shown in FIG. 4 and further showing the feature of the outwardly displaceable anchor associated with an embedded stem location and which is actuated by a rotatable input applied to a screw incorporated into a rim surface location of the implant assembly.

FIGS. 4 and 5A illustrates both partially exploded and assembled views, generally at 10, of the combined installation stem and exposed end supported and universally articulating and spherical shaped head which can be installed into a reconditioned and channel defined end face 1 of an upper femur (or upper thigh bone) 2 of a patient, and typically such as following reconditioned removal of the previously existing (and typically compromised or damaged) bulbous shaped head of the upper femur 2, this further illustrated at 4 in phantom (FIG. 4) and which is normally accomplished with the use of an appropriate medical saw or like power reciprocated or chain drive, as well as manually reciprocated instrument, see at 3 in FIG. 4. The upper femoral end is therefore reconditioned so that it exhibits a smoothed and generally annular shaped receiving face 1, and which can include a bored out and interior extending passageway within the femur 2.

A replacement implant assembly 10 is subsequently installed upon the reconditioned femur as a replacement for the original ball portion 4 and includes an integrated assembly exhibiting a generally elongated and arcuate stem 12 which is supported within the interior passageway associated with the upper femur bone 2. The stem 12 can be adhesively cemented within the femur bone interior (such as through the application of a polymethylmethacrylate) and it is further envisioned that an inner remote end of the stem 12 can be cored or otherwise recess machined, see as shown 13 in FIG. 5A, this in order to promote the in-growth of marrow within the and around the inserted end of the stem 12 and to improve long term anchoring support of the stein within the bone.

A generally spherical or ball shaped head 14 is integrally foamed with the stem 12 and, as shown, is separated by an interposed and annular surface exposed rim or 16 which defines an installation limit of the stem 12 within the conditioned and passageway defined bone interior of the femur 2 (see again FIG. 4). As will be described, the stem 12 and annular rim 16 are typically constructed of a softer material as opposed to the ball 14, however is subject to modification according to desired performance objectives.

A flexible and resilient ligament 18 is provided in extending fashion from a generally top central location of the ball 14, this further optionally exhibiting a slightly concave dimple or recess 20. The ligament 18 is mounted in generally linear projecting fashion from a top central location of the ball 14 and exhibits material properties of flexibility and resilience such as associated with a durable silicone or like flexible material. As further shown, the ligament exhibits a series of modified diameter portions, terminating in an outermost annular/tapered configuration 22 and which, as will be subsequently described, assists in mounting the ligament 18 in resistive engaging fashion within an associated internal seating recess (as defined at 31 in FIG. 10) defined in a cup shaped member 24.

Figure 12:
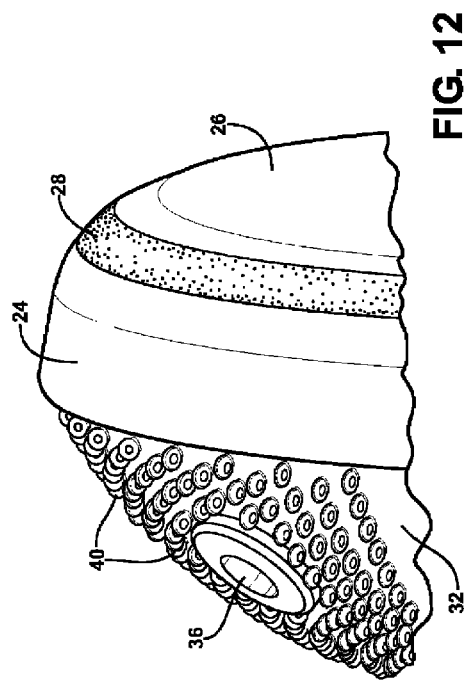
FIG. 12 is a further enlarged partial of the cup shaped support and illustrating the features of the bone growth locking texture exhibited on the three dimensional mounting face as well as the provision of an inner shock absorbing layer.

The cup shaped member 24, as with the implant body 10, exhibits any plastic, metal or admixture of material and includes a generally concave shaped surface 26 which supports the ball 14 in a seating and universally articulating fashion. The cup 24 further includes a softer and inner/arcuate absorbing layer 28 (see as best shown in FIGS. 11 and 12) extending between the inner concave face 26 and the rear convex face 32 and which in use absorbs any forces imparted by the ligament attached and seating spherical ball 14.

As shown, the concave and interior volume defining face is configured for receiving the flexible and resilient ligament 18 associated with the ball 14 in an undercut fitting and universally articulating permitting fashion. The cup shaped member 24 is in turn affixed to a previously reconditioned acetabulum socket 6 associated with an ilium bone 8, and in which a further central positioned hole (see as further shown at 9 in FIG. 10 and the formation of which will be better described in reference to the description of FIGS. 18 and 19) with an undercut feature is created for receiving a like configured and central projection 30 of the cup 24.

As is best illustrated in reviewing FIGS. 10 and 11 in combination, the configuration of the central arranged and rear extending mounting projection 30 of the cup 24 both seats within the undercut established hole 9 in the acetabulum, as well as defines a similarly configured inner aperture (again at 31) for receiving the ligament 18 in a likewise resistive fitting/undercut defining arrangement for seating the spherical ball 14 in a defined universally articulating and supported fashion within and against the concave inner cavity 26 established by the acetabulum secured cup 24. As further illustrated in reference to FIGS. 11 and 12, a rotated perspective view to that shown in FIG. 10 illustrates the central engaging projection 30 associated with the three dimensional convex mounting face 34 of the cup shaped support 24 for engaging within the previously drill undercut recess 9, the central projection 30 also defining the interior passageway 31 (FIG. 10) and which is understood to exhibit a suitable inner and annular configured profile for receiving and resistively seating the outermost extending and engaging end 22 of the ligament 18 in resistive fitting fashion.

Figure 1A:
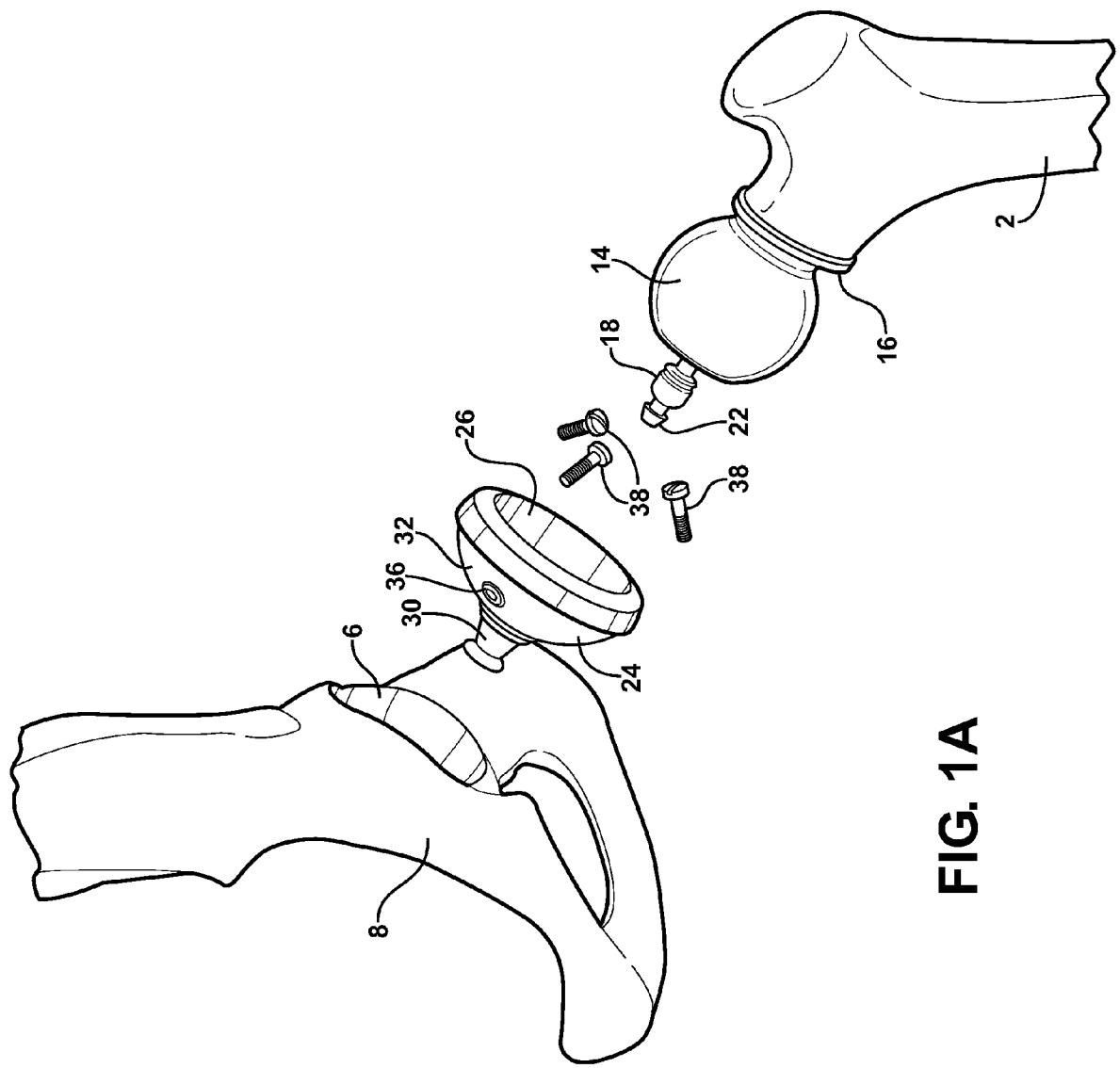
FIG. 1A is a partially exploded view of the hip socket implant assembly including a spherical shaped ball mounted to a reconditioned end of an upper femur, in combination with a stationary support anchored within a associated acetabulum socket defined in the lateral base of the ilium and between the pubis and ischium branches, the ball further exhibiting a flexible ligament extending therefrom which engages the cup shaped support as a single and universally articulating assembly.
Figure 13:
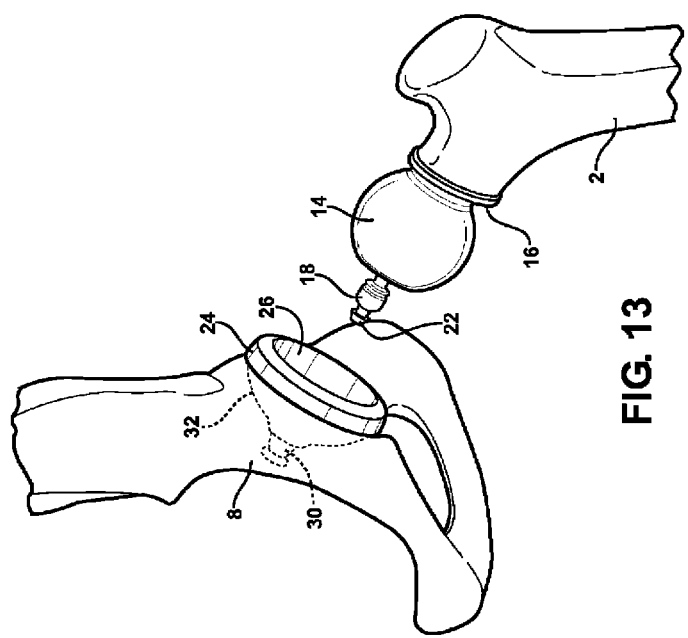
FIG. 13 is an illustration similar to that shown in FIG. 1A and in which the cup shaped spacer is illustrated in phantom mounted configuration relative to the reformed acetabulum and prior to engagement of the resilient ligament extending from the spherical shaped ball.

As further shown in FIG. 10, an array pattern of additional drill holes 11 are created in the acetabulum socket (this according to the template of FIGS. 8 and 9) and which align with a further plurality holes 36 (see FIG. 10) arranged in an array pattern in the body of the cup shaped support 24. As further shown in FIGS. 1A and 1B, a plurality of threaded fasteners 38 are provided and install through the holes 36 to mount the cup 24 to the reconditioned socket 8. With particular reference to FIG. 13, it is further understood and appreciated that both the undercut defining profile established by hole 9 in the acetabulum and the additional formed drill holes 11 collectively provide all of the required holding forces to the cup 24 and do not extend to the rear facing side of the ilium bone 8.

FIG. 12 is a further enlarged partial of the cup shaped support and illustrating the features of the bone growth locking texture, see as representatively defined by ring portions 40 exhibited on the three dimensional rear convex mounting face 32 of the cup 24, these promoting the long term growth of bone marrow following affixation of the cup 24 to the previously reformed acetabulum surface 6 (as will be subsequently described) and which can be used in combination with such as a bone engaging adhesive for promoting long term stability to the installation. Aside from the ring portions 40, it is again understood that alternately shaped projections, patterns and the like can be exhibited upon the exposed convex surface of the cup and to promote long term bone growth, such complementing the use of an intermediate term adhesive and the mounting fasteners 38 for maintaining the cup in position while aggregating and normal bone growth provides additional anchoring in place to the acetabulum.

As with the cup 24, it is further understood that the annular extending flange 16 associated with the femur implant 10 (FIG. 4A) can be constructed of a softer grade plastic or other material as compared to either or both the stem 12 or ball 14, this assisting in more easily shaping and form fitting of the flange 16 about the exposed reconditioned surface of the upper femur 2. As further illustrated in both FIGS. 4 and 5A, the feature of an outwardly displaceable anchor 42 is shown associated with an embedded stem 12 location, and which is actuated by a rotatable input such as to a rotatable screw 44 incorporated into the annular rim surface location 16 of the implant assembly.

A series of interior and interconnected linkages, see as represented by flexible shaft 46, communicates the rotatable input applied to the screw 44 (this such as by a tool or other suitable keyed implement) to an end-rotatable component, see further shown at 48 and which is operated by the turning of the selected linkage 46, to in turn outwardly displace the anchor 28 (such as which can be influenced by a suitable ratcheting or inter-teethed arrangement) outwardly and in biasing contact with the interior of the upper thigh bone. As is further shown, the forward/upward angle associated with the upper surface configuration of the anchor 42 is such that, upon it being actuated outwardly and against the inner surface of the femur bone in communication with the inner passageway, the stein 12 and annular flange 16 are caused to be biased inwardly within the femur 2 and further so that the annular surface flange 16 is pulled tight against the reconditioned femur surface 1 as shown in FIG. 4.

Figure 1B:
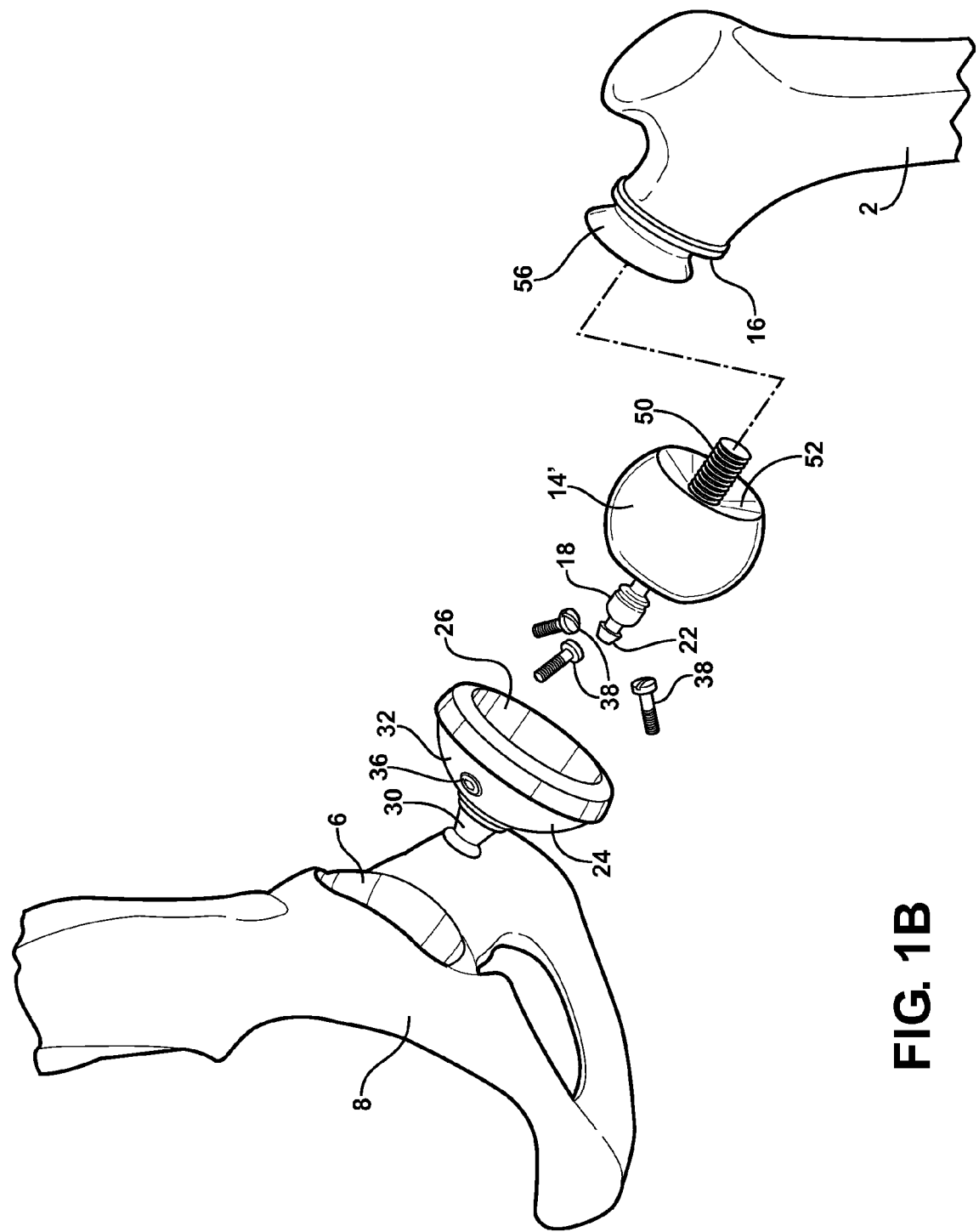
FIG. 1B is a successive partially exploded view largely similar to that shown in FIG. 1A and further illustrating the two piece nature of the spherical ball which is separable via a threaded shaft fastener from a stem in turn mounted within the upper femur reconditioned end face.
Figure 5B:
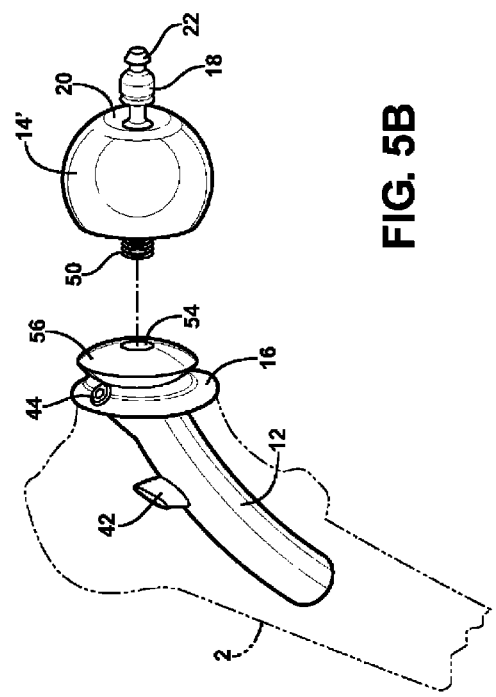
FIG. 5B is a partially exploded view of FIG. 5A and, in combination with FIG. 1B, illustrating from another angle the threadably engageable nature of the spherical shaped ball to an associated mounting surface of the femur secured stem which further exhibits an annular extending end flange surface secured over the reconditioned end of the femur.

The actuation linkage demonstrated is intended to show only one of a number of potentially varying mechanisms for outwardly displacing an anchor for providing an additional degree of fixed support to the stem, this in addition to either or both the use of adhesives for cementing the stem 12 to the inner passageway defining surfaces of the femur bone and/or the notching or inner end coring of the stem in order to promote the natural growth of bone marrow. It is further understood that various combinations of some or all of these implant retaining features can be utilised in order to secure the implant assembly in place upon the reconditioned bone end and concurrent with FIGS. 1B and 5B are illustrations of a slight variant of the implant assembly 10 of FIG. 5A, and in which the one piece ball 14 and supporting stem 12 of FIG. 11 is reconfigured into a pair of threadably or otherwise inter-engageable components. This includes a modification of the ball 14' having an externally threaded shaft end 50 extending from an inwardly concave/dimpled base surface 52 (see again FIG. 1B) which is threadably engaged with an inner threaded surface 54 associated with a mating interior passageway communicating with the stem 12 and in proximity to a tapered annular projecting support 56 which mates with the dimpled underside 52 of the ball 14 to provide support to said ball upon said stem and to further facilitate releasably securing the ball 14 in the manner shown in FIG. 2A.

In this fashion, a damaged ball 14 can be removed and replaced, such as during a follow up surgical procedure, and without the requirement of retrieval/removal of the interior anchored stem 12. It is also understood that the flange 16 can be constructed of a softer grade plastic as opposed to the ball 14 and in so that it, along with the stem 12, can better adapt to the inner shape or contour of the femur 2.

Figure 6:
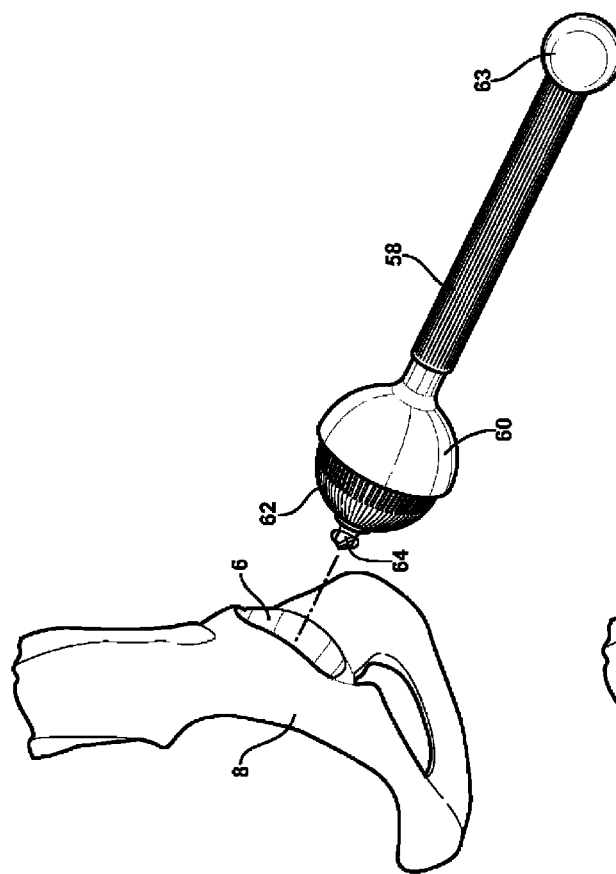
FIG. 6 is an illustration of a portable and band held rotary ball shaped grinder, such as can be provided as an attachment secured to a rotary drill motor and which includes built in vacuum retrieval of debris, the grinder being utilized in situ within the patient for refashioning/resizing the associated acetabulum socket defined in the lateral base of the ilium and between the pubis and ischium branches.

Referring now to FIG. 6 illustrated is a portable and hand held rotary ball shaped grinder, such as shown at 58 and which can be provided as a self contained and powered unit or alternatively as an attachment secured to a separate rotary drill motor (not shown). The rotary grinder 58 exhibits a hand held gripping body and, at a forward end, terminates in a generally hemispherical seating portion 60 upon which is rotatably supported (such as via a drive shaft extending longitudinally along an interior of the tool from a powered input located in the handle) a further hemispherical shaped and rotating grinder bit 62, this in turn being rotated by the inner drive shaft.

As is further illustrated, the hemispherical shaped grinder bit 62 exhibits a plurality of individual incising blade portions which are arranged in a longitudinal arrayed pattern. Upon being placed over the acetabulum socket 6 of the ilium bone 8 (see FIG. 7), this again being defined in the lateral base of the ilium and between the pubis and ischium branches, the grinder 58 is activated in order to progressively shave bone from the acetabulum 6, causing its socket profile to eventual match the exterior profile of the hemispherical bit 62 in order to create a three dimensional open interior. An open interior (not shown) established between the hemispherical shaped base 60 and attached hemispherical bit 62 and provides for collection of bone shavings and debris which pass through likewise longitudinally extending apertures integrally defined in the bit 62, these subsequently being vacuum removed from the grinding head for storage within such as a waste chamber located in a rear handle situated location, see as shown at 63, or other portion of the grinder 58 for subsequent emptying.

The grinder 58 further includes a central projecting bit 64 (see also FIGS. 18 and 19) for creating a hole in a base of the acetabulum 6. A subsequently outwardly protruding and centrally located pair of undercut profile defining blades 66 and 68 (the term blade also generally understood to encompass and include bits or other abrading portions which are exerted against the inner facing wall of the previously formed hole in order to achieve a desired undercut profile) are provided and which are configured within the central projecting bit 64 and which are incrementally actuated for creating a successive undercut configuration within the access hole 9 (again FIG. 10) formed in the reground acetabulum, and which is subsequently and resistively engaged by an associated annular ring projection associated with the central base projection 30 of the stationary cup 24.

Referring again to FIGS. 18 and 19, and following completion of the initial reshaping of the acetabulum and formation of the initial drill hole within the ilium bone interior by the grinder tool bit 64, a secondary and interior shaft, at 70, seated within a linear passageway defined in said bit 64 is actuated to linearly/outwardly displace, such as via gear drive components 72 built into the upper grinder bit 62 housing and which coacts with a suitable mating teethed or other desirable pattern formed in a base of the inner displaceable shaft 70. The upwardly displacing shaft, at this point, contacts the pair of laterally displaceable undercut defining bits 66 and 68 previously referenced via underside disposed tapers, see at 74 and 76.

The bits 66 and 68 are seated within lateral passageways defined proximate a tip of the bit 64 and, upon the inner shaft 70 being upward displaced, its pointed tip 78 causes the secondary lateral bits 66 and 68 to be laterally displaced outwardly in an incremental and progressive fashion, in response to progressive undercut machining of bone and in order to create the desired undercut profile. Following completion of the undercut machining step, the inner shaft 70 is retracted and the lateral bits 66 and 68, via their outer profiles, are caused to recess retract upon exerting a removal force to the overall bit body and at which point the bits 66 and 68 abut against the undercut defining ledges which in turn cause them to retract to the position originally shown in FIG. 18.

Given the precise and in situ nature of the bone machining process, it is further desirable to provide the acetabulum reshaping, concurrent formation of the initial drill hole, and subsequent formation of secondary undercut hole using the same tool and in a quickly succeeding nature, with the undercut being located at any lengthwise internal position of the initial drill hole in order to correspond to the configuration of any subsequently installed retaining post or anchor. That said, it is also envisioned and understood that the feature of the undercut formation can be provided by a separate drill bit with spring out portions such as described above or the like, and which may be inserted within a template defined aperture following completion of the primary drill hole by a more conventionally configured bit.

Figure 7:
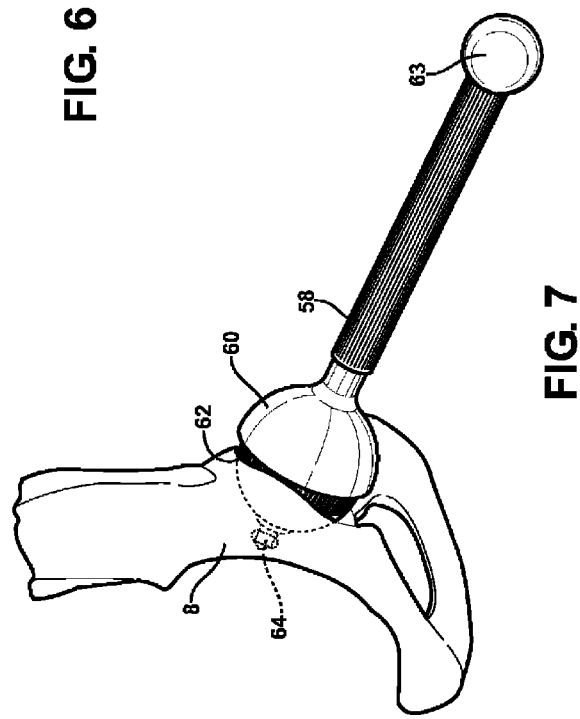
FIG. 7 is a succeeding illustration to FIG. 6 and showing the grinder in a substantially acetabulum reforming operation and illustrating the reshaping of the acetabulum socket and formation of the inner anchor retaining drill hole within the interior of the bone and without breaching the rear side, the grinder further including a subsequently outwardly protruding and centrally located center blades for creating a successive undercut configuration within the reground acetabulum, such as for engaging a successively installed socket anchor.

Referring now to FIGS. 8 and 9, illustrated of a successive installation step following the application of the combination rotary grinder and undercut defining, hole of FIGS. 6 and 7 in the arthroplasty procedure, and by which a drill fixture template 80 is mounted to the previously refashioned cavity 6, the fixture 80 including an array of apertures, such as depicted at 82, for use in creating the further drill holes identified at 11 in FIG. 10 in order to create a pattern within the recessed interior of the previously reformed socket.

The a drill fixture or template 80 exhibiting a generally disk shape with edge extending engagement tabs 84 is provided and is temporarily mounted via the tabs 84 engaging specified surface locations of the ilium bone 8 in order to cover the previously refashioned acetabulum cavity. A specially modified and combination drill with a powered extending bit 86 is provided in order to create a precise drill pattern within the recessed interior of the previously reformed socket 6.

As with the rotary grinder 58, the modified drill and bit 86 can be self-powered or, as shown at 88 in FIG. 8A, can be provided as a bit attachable to a separate hand-held and powered unit. As with the rotary grinder 58, the further modified drill 86 includes a hand held body which vacuum evacuates and stores, such as within an internal waste chamber not shown but evident from the body shown at 86 in FIG. 8, bone debris created from the internal holes drilled through the aperture pattern in the template 80 and, upon subsequent removal of the template 80 and installation of the cup shaped support 24, the additional fasteners 38 are installed through the mating hole patterns identified at 36 in cup 24 and the holes 11 defined in the reformed acetabulum.

Referring now to FIGS. 15, 16 and 17, illustrated are examples respectively shown at 90, 92 and 94 of a variety of different types of recess anchors, each of which being constructed of a durable and flexible/expandable plastic in a generally balloon or condom-like shape within an open bottom end and which are sized so as to be installed within the previously formed drill hole with undercut profile according to the forming procedures of FIGS. 6, 7, 18 and 19 utilizing the main rotary drill 58. Each of the recess anchors further incorporate a protruding or expanding barb, see respective profiles 96 for FIG. 15 (matching laterally displaceable bits 66 and 68), at 98 for FIG. 16 (incorporating pairs of dovetail undercut patterns for engaging linearly spaced undercut profiles formed in the previous drill hole via a suitable drill tool or the manipulation of a tool which relocates the undercut bits to a secondary location) and finally at 100 for FIG. 17 (generally balloon shaped profile for seating within an enlarged and more bulbous shaped undercut profile achieved with a suitable tool).

As further shown, the open bottom ends of the individual configured anchors 90, 92 and 94 are each configured with an internal pattern or the like profile, in each instance identically represented by inner profile established at 102. Upon pre-installing any of the anchors 96, 98 or 100 into the centrally formed drill hole 9 with undercut profile (see FIG. 10) according to the resistive fitting of the anchor into the previously created undercut profile, the exposed underside profile 102 is configured so as to in turn receive the central extending and annular rim defining projection 30 of the cup 24 in a likewise resistive and undercut engaging fashion. It is further understood that any kind of anchor, screw or fastener, such as further exhibiting any of a plastic, metal or combined material, can also be substituted for mounting the cup 24 to the reformed acetabulum 6.

Additional to the ligament 18 established between the spherical ball 14 and the cup interior 26, it is further understood that additional or ancillary ligament or connective structure can be provided and which is understood and envisioned to include any type of naturally forming and/or artificial ligament structure, such as replicating the traditional five types of ligaments of which four are extracapsular (iliofemoral, ischiofemoral and pubofemoral (2)) and one intracapsular (liagmentum teres). Also not shown but understood to be present both in the presently disclosed structure and succeeding description of the associated arthroplasty procedure are the features of reconstructed vein, nerve and muscle connections, these borrowing from both existing and novel techniques and procedures for creating an effective and durable artificial hip implant.

Having described my invention, other and additional preferred embodiments will become apparent to those skilled in the art to which it pertains, and without deviating from the scope of the appended claims.

I claim:

1. A hip implant assembly, comprising:
 a ball from which extends an elongated stem, an annular defining flange separating said ball from said stem and adapted to about an exterior surface of a reconditioned femur bone upon inserting said stem within an interior defined passageway associated with the femur;
 a flexible ligament extending from said ball; and
 a cup shaped member adapted to secure to a reconditioned acetabulum of an ilium bone, an interior passageway defined in said cup engaging an extending end of said ligament, concurrent with a concave inner surface of said cup providing universally articulating and seating support to said ball.

2. The invention as described in claim 1, further comprising said stem adapted to being adhesively cemented within the femur bone interior.

3. The invention as described in claim 1, further comprising an inner remote end of said stem being cored or otherwise recess machined in order to promote the in-growth of marrow within the and around said stem.

4. The invention as described in claim 1, further comprising each of said ball, stem flange and cup shaped member being constructed of any type of plastic, metal or admixture.

5. The invention as described in claim 1, said cup shaped member further comprising a softer and inner/arcuate absorbing layer adapted to extend in embedded fashion between an inner facing surface and an outer facing surface adapted to seat against the acetabulum socket.

6. The invention as described in claim 1, further comprising said annular extending flange constructed of a softer grade material than said stem and ball to assist in shaping and form fitting about an exposed reconditioned surface of the upper femur.

7. The invention as described in claim 1, further comprising an outwardly displaceable anchor within said stem which is actuated by a rotatable input to a screw surface mounted in said annular flange, a series of interior and interconnected linkages are incorporated into said body and transfer a rotatable input applied to said screw to outwardly displace said anchor into biasing contact with the interior of the femur, causing said flange to be drawn tight against the reconditioned surface of the femur.

8. The invention as described in claim 1, further comprising said ball and supporting stem configured as a pair of threadably engageable components, said ball including an externally threaded shaft end which is threadably engaged with an inner threaded surface associated with a mating interior passageway of said stem and in proximity to said annular flange.

9. The invention as described in claim 8, said ball exhibiting an inwardly concave surface from which extends said externally threaded shaft, a tapered annular projection extending from said annular defined flange within which is defined said inner threaded surface and providing seating support to said ball.

10. The invention as described in claim 1, said cup further comprising a central engaging projection associated with a three dimensional convex mounting face for engaging within a previously drill undercut recess formed in the acetabulum.

11. The invention as described in claim 10, further comprising a pattern of holes formed in said cup in surrounding fashion about said central projection and adapted to align with additional drill holes created in the acetabulum, a plurality of fasteners installing through the holes to assist in mounting said cup to the reconditioned socket.

12. The invention as described in claim 10, further comprising a flexible anchor adapted to resistively fit within the drill undercut recess formed in the acetabulum, said anchor exhibiting an enlarged resistance engaging end which is linearly displaced into and in resistive engaging contact with the previously defined undercut recesses formed in the acetabulum socket, an open bottom of said flexible anchor receiving said cup engaging portion in likewise resistive fitting fashion.

13. The invention as described in claim 10, said cup further comprising a plurality of texture defining projections exhibited on said convex mounting face for promoting long term growth of bone marrow following affixation of said cup to the acetabulum.

14. The invention as described in claim 1, further comprising said ligament extending from a generally top central location of said ball.

15. The invention as described in claim 14, said ligament further comprising at least one modified diameter portion and terminating in an outermost annular configuration for engaging with said interior passageway in said cup.

16. The invention as described in claim 14, said ligament having a specified shape and size and exhibiting the material properties of flexibility and resilience.

17. A hip implant assembly, comprising:
   a ball;
   an elongated stem connected to said ball and which is adapted to install within a reconditioned femur bone upon inserting within an interior defined passageway associated with the femur;
   a flexible ligament extending from said ball and exhibiting an outermost and annular configured portion; and
   a cup shaped member adapted to secure to a reconditioned acetabulum of an ilium bone, an interior passageway defined in said cup and engaging said outermost annular portion of said ligament, concurrent with a concave inner surface of said cup providing universally articulating and seating support to said ball.

* * * * *